United States Patent [19]

Herskowitz

[11] Patent Number: 5,652,193
[45] Date of Patent: Jul. 29, 1997

[54] METHOD FOR HYDROCARBON SYNTHESIS REACTIONS

[75] Inventor: Mordechay Herskowitz, Beer-Sheva, Israel

[73] Assignee: Exxon Research and Engineering Company, Florham Park, N.J.

[21] Appl. No.: 559,929

[22] Filed: Nov. 17, 1995

Related U.S. Application Data

[63] Continuation of Ser. No. 106,312, Aug. 13, 1993, abandoned, which is a continuation of Ser. No. 951,027, Sep. 24, 1992, abandoned, which is a continuation of Ser. No. 331,035, Mar. 29, 1989, abandoned, which is a continuation of Ser. No. 914,781, Oct. 3, 1989, abandoned.

[51] Int. Cl.$^6$ .............. B01J 23/56; B01J 23/00
[52] U.S. Cl. ...................... 502/332; 502/325
[58] Field of Search ........................ 502/325, 332

[56] References Cited

U.S. PATENT DOCUMENTS

| | | |
|---|---|---|
| 2,512,608 | 6/1950 | Buchman . |
| 3,549,556 | 12/1970 | Diene . |
| 4,042,614 | 8/1977 | Vannice et al. . |
| 4,171,320 | 10/1979 | Vannice et al. . |
| 4,477,595 | 10/1984 | Madon . |
| 4,559,364 | 12/1985 | Wood et al. . |
| 4,567,205 | 1/1986 | Arcuri et al. . |
| 4,568,663 | 2/1986 | Mauldin . |
| 4,599,481 | 7/1986 | Post et al. . |
| 4,637,993 | 1/1987 | Van Erp et al. .............. 518/715 |
| 4,962,078 | 10/1990 | Behrmann et al. ............ 502/325 |
| 4,977,126 | 12/1990 | Mauldin et al. .............. 502/332 |
| 5,036,032 | 7/1991 | Iglesia et al. ................. 502/350 |

FOREIGN PATENT DOCUMENTS

| | | |
|---|---|---|
| 2105604 | 3/1983 | United Kingdom . |
| 2024246 | 1/1988 | United Kingdom . |

OTHER PUBLICATIONS

Tucci et al, Hydrocarbon Processing, Feb. 1979, pp. 123–125

Dixit et al, Ind Eng Chem Pwos Des Dev 1983, pp. 1–9, 22.

Evason et al J of Catel. 53 186–197, 1978.

*Primary Examiner*—Glenn A. Caldarola
*Assistant Examiner*—Elizabeth D. Wood
*Attorney, Agent, or Firm*—Ronald D. Hantman

[57] ABSTRACT

A method for producing hydrocarbon synthesis catalyst pellets which include a solid or inert core and a coated layer of porous support impregnated with a catalytic metal, the method provides catalysts which optimize the CO conversion and minimizes selectivity to $CH_4$.

5 Claims, 3 Drawing Sheets

METHOD FOR HYDROCARBON SYNTHESIS REACTIONS

"This application is a continuation of application Ser. No. 08/106,312, filed Aug. 13, 1993 and now abandoned, which is a continuation of application Ser. No. 07/951,027, filed Sep. 24, 1992 and now abandoned, which is a continuation of application Ser. No. 07/331,035, filed Mar. 29, 1989 and now abandoned, which is a continuation of application Ser. No. 06/914,781, filed Oct. 3, 1986 and now abandoned.

BACKGROUND OF THE PRESENT INVENTION

This invention relates to a method for converting hydrogen and carbon monoxide to heavy hydrocarbons in a fixed bed reactor by a catalytic reaction where the catalyst pellet is designed so as to optimize the CO conversion and methane selectivity. Selectivity to methane is the percentage of the total CO moles converted.

A metal catalyst (e.g. cobalt or ruthenium) on a support (e.g., titania or silica) which may be promoted by different metals (e.g., rhenium, hafnium and others) are used for synthesis of heavy hydrocarbons from a mixture of carbon monoxide and hydrogen. The principal reaction may be expressed as:

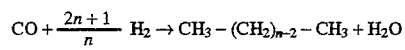

where the distribution of the hydrocarbon products can be approximated by the Flory-Schultz expression. The fraction of oxygenates and olefins in the product is small.

An important consideration in the development of the hydrocarbon synthesis process is to minimize the production of light hydrocarbons ($C_1$–$C_4$), especially of methane. The fraction of methane in the product exceeds that predicted by the Flory-Schultz distribution.

Another important consideration is to maximize the productivity, defined as the number of CO moles converted per unit time and reactor volume, so as to minimize the volume of the reactor in which the reaction is carried out.

Both considerations have been met with available catalyst powder of the size 80–140 mesh (approximately 0.15 mm in diameter). However, additional factors should be considered in the design of a fixed bed reactor; namely, the pressure drop in the reactor, and the removal of the heat generated by the reaction.

These require the design of catalyst pellets which retain the properties of the powder catalyst (80–140 mesh) but are larger in size (>1.0 mm). However, since the reactants have to diffuse through liquid-filled pores, the longer diffusion path may create concentration gradients within the pellet. Such gradients alter the hydrogen to carbon monoxide ratio in the pellet due to the lower diffusivity of the latter. As a result the selectivity to methane, which depends on this ratio, increases considerably. Furthermore, since the rate of reaction depends on the concentration of the two reactants, the productivity is smaller in a pellet than in powder.

Because the pellets have to be used in a fixed bed reactor, the design of the catalyst pellet has to be directed toward minimizing the methane. selectivity and maximizing the productivity, where productivity is defined as the number of CO moles converted per unit time and reactor volume. The catalyst of the present invention is designed to achieve this purpose.

SUMMARY OF THE PRESENT INVENTION

The present invention is a method for converting hydrogen and carbon monoxide to heavy hydrocarbon in a fixed bed reactor by a catalytic reaction. The method includes contacting the hydrogen and carbon monoxide in the reactor at reaction conditions with a supported catalyst pellet. The support includes an inert or hollow core and an outer layer of porous inorganic refractory oxide. The outer layer has a thickness determined so as to optimize CO conversion to heavy hydrocarbons so that conversion to methane is maintained at a predetermined level. The thickness is-determined by relating the rate of diffusion of the CO and the hydrogen to a rate of reaction in the porous inorganic oxide for a predetermined support geometry, partial pressures, and temperatures. The support may take on many shapes, e.g., sphere, ring or semi-circle.

A metal catalyst (e.g. cobalt or ruthenium) on a support (e.g., titania or silica) promoted by different metals (e.g., rhenium, hafnium and others) are used for synthesis of heavy hydrocarbons from a mixture of carbon monoxide and hydrogen.

The concentrations of both hydrogen and carbon monoxide decrease as they diffuse into the pellet due to significant mass transfer resistance inside the pores. The global rate of CO conversion in the pellet decreases. Furthermore, the methane production rate increases which is a result of its dependency on the ratio between the hydrogen to CO concentration which increases in the pellet. This ratio increases if the parameter $\gamma$ (see equation 11 below) is less than unity. This behavior was observed in Co or Ru catalysts supported on titania, silica or alumina.

At a certain depth in the pellet, the hydrogen to CO ratio reaches values which cause most of the CO to be converted to methane which is detrimental to the process. This depth which is called the optimum rim thickness can be determined from the pellet model. Increasing the rim thickness diverts most of the marginal CO conversion to methane while decreasing the rim thickness decreases the CO conversion significantly. Therefore, for an optimal operation, the optimal rim thickness should be determined.

As will be discussed below with respect to FIGS. 2 and 3, it is not possible to simultaneously maximize CO conversion and minimize methane conversion. However, it is possible to choose a rim thickness so as to optimize CO conversion to heavy hydrocarbons.

The process of the present invention carried out at a rate of CO conversion to hydrocarbons such that the percentage of methane production is maintained at a predetermined low level so as to make, the entire process useful and practical.

As the rim thickness increases above the optimal rim thickness, the marginal increase in CO conversion is accompanied by an increase in the percentage of methane production in the converted carbon monoxide. This is observed in FIG. 2 and 3 discussed below. At the optimal rim thickness, most of the increase in CO conversion goes into methane production. Since an object of the present invention is to limit methane production in the converted CO, a rim thickness must be chosen at about this value.

The supported catalyst may be fabricated by a number of different methods known in the art, see e.g., Scientific Basis For the Preparation of Heterogenous Catalyst, Preprints of the Fourth International Symposium, Sep. 1–4, 1986, Louvain-La-Nueve, Belgium.

DESCRIPTION OF THE PREFERRED EMBODIMENT

Figure 1:
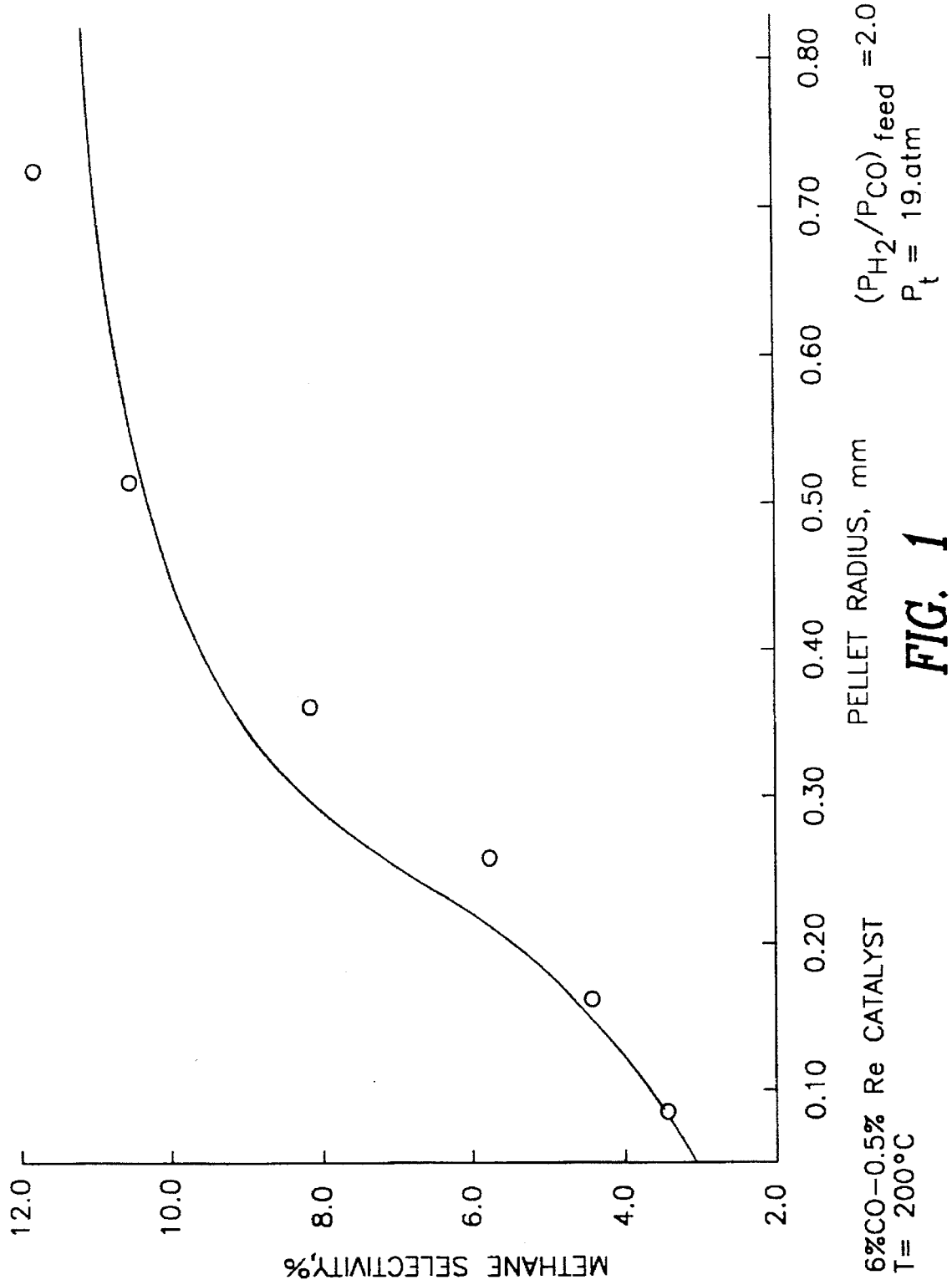
FIG. 1 shows the model predictions for methane selectivity as a function of pellet radius compared with experimental data.

The two reactants, hydrogen and carbon monoxide, diffuse in the liquid filled pores to reach the active metal sites on the support. The function of the support is to increase the surface area which is equal to about 20 m²/g in this case. At steady-state, the fluxes of the two reactants in the pores are equal (since there is no accumulation):

$$\beta D_{e,CO}\frac{dC_{CO}}{d\chi} = D_{e,H}\frac{dC_H}{d\chi} \qquad (1)$$

where the flux is expressed as a product of the effective diffusivity $D_e$ and the concentration gradient. $\beta$ is the stoichiometric coefficient which is equal to 2.07 for the hydrocarbon synthesis reaction. The ratio of the gradients depends on the ratio of the two diffusivities. Since the diffusivity of hydrogen is greater than that of carbon monoxide, the hydrogen to carbon monoxide ratio is expected to increase, moving from the pellet surface towards its center.

A differential mass balance inside the pellet pores for the carbon monoxide (which is the limiting reactant, namely it is depleted before the other reactant) yields:

$$D_{e,CO}\frac{1}{\chi^s}\frac{d}{d\chi}\left(\chi^s\frac{dC_{CO}}{d\chi}\right) = \rho_p r_{CO} \qquad (2)$$

where X is the radial position measured from the external surface toward the center, $\rho_p$ is the pellet density $C_{co}$ is the CO concentration in the liquid-filled pores and $r_{co}$ is the intrinsic rate of reaction on the active sites. s is equal to two for a sphere and to unity for a cylinder. This analysis has been carried out for a sphere or a cylinder. However, the analysis can be easily extended to other shapes. For example, rims having a ring shape or a semi-circular shape may be used.

The boundary condition on the external surface is:

$$C_{co}=P_{co,b}/H_{co} \quad X=X_s \qquad (3)$$

where $P_{co,b}$ is the CO partial pressure in the bulk gas phase and $H_{co}$ is the Henry's law constant. The other boundary condition is set in two cases:

1. inert core $$\frac{dC_{CO}}{d\chi}=0 \quad \chi=\chi_i \qquad (4)$$

2. hollow core $$C_{co}=P_{co,b}/H_{co} \quad X=X_i \qquad (5)$$

In the deviation of the boundary conditions it is assumed that the external mass transfer resistance is negligible. This assumption was tested both experimentally and theoretically. Furthermore, the pellet is assumed to be isothermal, based on calculations which indicated temperature gradients less than 0.1° C., as expected for liquid-filled porous catalysts.

Equation (2) is general for any reaction with diffusion, while the rate of reaction depends on the catalyst system. The intrinsic rate expression (free of internal or external mass transfer resistance) for catalyst systems such as cobalt or ruthenium on titania or silica can be written as:

$$r_{CO}=k_1\exp\left(-\frac{E_1}{RT}\right)\frac{P_{CO}^1 P_H^b}{(1+k_2P_{CO}+k_3P_H)^2} \qquad (6)$$

The values of $k_1$, $k_2$, $k_3$, $E_1$, a, b and c are calculated from kinetic rate data obtained in laboratory reactors. The kinetic parameter $k_1$ usually depends only on the metal concentration on the support. However, in certain cases such as cobalt on titania, it is also a function of the water partial pressure:

$$k_1=A\frac{1+k_4P_{H_2O}}{1+(k_5P_{H_2O})^2} \qquad (7)$$

where A is the activity of the catalyst.

Equation (6) can be expressed in terms of the CO and $H_2$ concentrations using the Henry's law:

$$C_{co}=P_{co}/H_{co}; \quad C_H=P_H/H_H \qquad (8)$$

Furthermore, the $H_2$ concentration can be expressed in terms of the CO concentration by integrating equation (1) to give $$C_H=\frac{P_{H,b}}{H_H}-\frac{\beta D_{e,CO}}{D_{e,H}}\left(\frac{P_{co,b}}{H_{co}}-C_{co}\right) \qquad (9)$$

or $$\frac{H_H C_H}{P_{H,b}}=1-\gamma\left(1-\frac{H_{co}C_{co}}{P_{co,b}}\right) \qquad (10)$$

where $$\gamma=\frac{\beta D_{e,CO}}{D_{e,H}}\frac{H_H}{H_{co}}\frac{P_{co,b}}{P_{H,b}} \qquad (11)$$

Substituting equations (6) and (10) into equation (2) and expressing the equation in dimension-less form yields the dimensionless number $$\phi=(\chi_s-\chi_c)\left[\frac{\rho_p k_1\exp\left(-\frac{E_1}{RT}\right)H_{co}P_{H,b}}{D_{e,co}(k_2P_{co,b})^c}\right]^{1/2} \qquad (12)$$

$\phi$, called the Thiele modulus, is the ratio between the maximum rate of reaction and the maximum rate of diffusion. If $\phi\gg1$ the process is diffusion limited while for $\phi\ll1$ the process is kinetic limited. Since $\phi$ is directly proportional to the thickness of the active layer or rim, diffusion is important in pellets and negligible in powder. The other factors affecting $\phi$ are the partial pressures, temperature and the catalyst activity (metal loading).

$\gamma$ expresses the ratio between the maximum rate of diffusion of the two reactants. If $\gamma=1$, the ratio of carbon monoxide to hydrogen remains unchanged in the pores while for $\gamma<1$ this ratio decreases.

Equation (2) is solved to yield the concentration profiles in the pores of the pellet. Then the concentration profiles are integrated over the volume of the pellet to calculate the effectiveness factor which is the ratio of the actual rate of reaction (called the global rate of reaction) and the maximum rate reaction calculated at the surface conditions:

$$\eta_{CO} = \frac{\frac{1}{V} \int_{V_P} r_{CO} dV}{r_{CO}(P_H, P_{CO}, P_{H_2O})} \quad (13)$$

The same concentration profiles are integrated using the rate of methane production rate $r_{CH_4}$ to yield the effectiveness factor for methane $$\eta_{CH_4} = \frac{\frac{1}{V_P} \int_{V_P} r_{CH_4} dV}{r_{CH_4}(P_H, P_{CO}, P_{H_2O})} \quad (14)$$

$r_{CH_4}$ was also obtained from kinetic measurements:

$$r_{CH_4} = k_4 \exp\left(\frac{-(E_2 - E_1)}{RT}\right) \frac{P_H}{1 + k_2 P_{CO} + k_3 P_H} r_{CO} \quad (15)$$

Finally, $\eta_{co}$ and $\eta_{CH_4}$ are employed in the reactor mass balance to calculate the carbon monoxide conversion and the methane selectivity. For simplicity, the reactor is assumed to be isothermal:

$$y_{CO,i} \frac{G_f}{M_i} \frac{dX_{CO}}{dZ} = \eta_{CO} \rho_B r_{CO} \quad (16)$$

$$y_{CO,i} \frac{G_f}{M_i} \frac{dX_{CH_4}}{dZ} = \eta_{CH_4} \rho_B r_{CH_4} \quad (17)$$

where $Y_{co,i}$ is the carbon monoxide mole fraction in the feed, $G_f$ is the mass velocity, $M_i$ is the molecular weight of the feed, $\rho_B$ is the bed density and $X_{co}$ and $x_{CH_4}$ are the carbon monoxide and methane conversion, respectively.

Although the fixed bed reactor is nonisothermal, thermal, the results presented here hold also in this case. Since the temperature increase never exceeds 30° F., the optimal rim thickness can be calculated at the average temperature in the bed.

Estimation of Effective Diffusivities

The carbon monoxide conversion and the methane selectivity were measured with a 6% Co–0.5% Re catalyst of different pellet sizes. The hydrogen to Co ratio in the feed was 2.0. Those data were used to estimate the carbon monoxide and hydrogen effective diffusivities following the procedure:

Values of $D_{e,CO}$ and $D_{e,H}$ were assumed;

The effectiveness factors $\eta_{CO}$ and $\eta_{CH_4}$ were calculated from equations (9) and (10) and the solution of equation (2) given the inlet conditions to the reactor;

Then the carbon monoxide conversion and the conversion to methane were calculated by integrating equations (16) and (17). Since the effectiveness factors are a function of the carbon monoxide, hydrogen and water partial pressures, the effectiveness factors were recalculated along the reactor as the partial pressures changed;

The methane selectivity was calculated from the ratio of the conversion to methane $X_{CH_4}$ and the carbon monoxide conversion $X_{CO}$;

The calculated carbon monoxide conversion and the methane selectivity were compared with the experimental values for the various pellet sizes; and The effective diffusivities are adjusted to give the best fit of the experimental data. A comparsion between the predictions and the data are given in FIG. 1 and Table 1.

EXAMPLE 1

Figure 2:
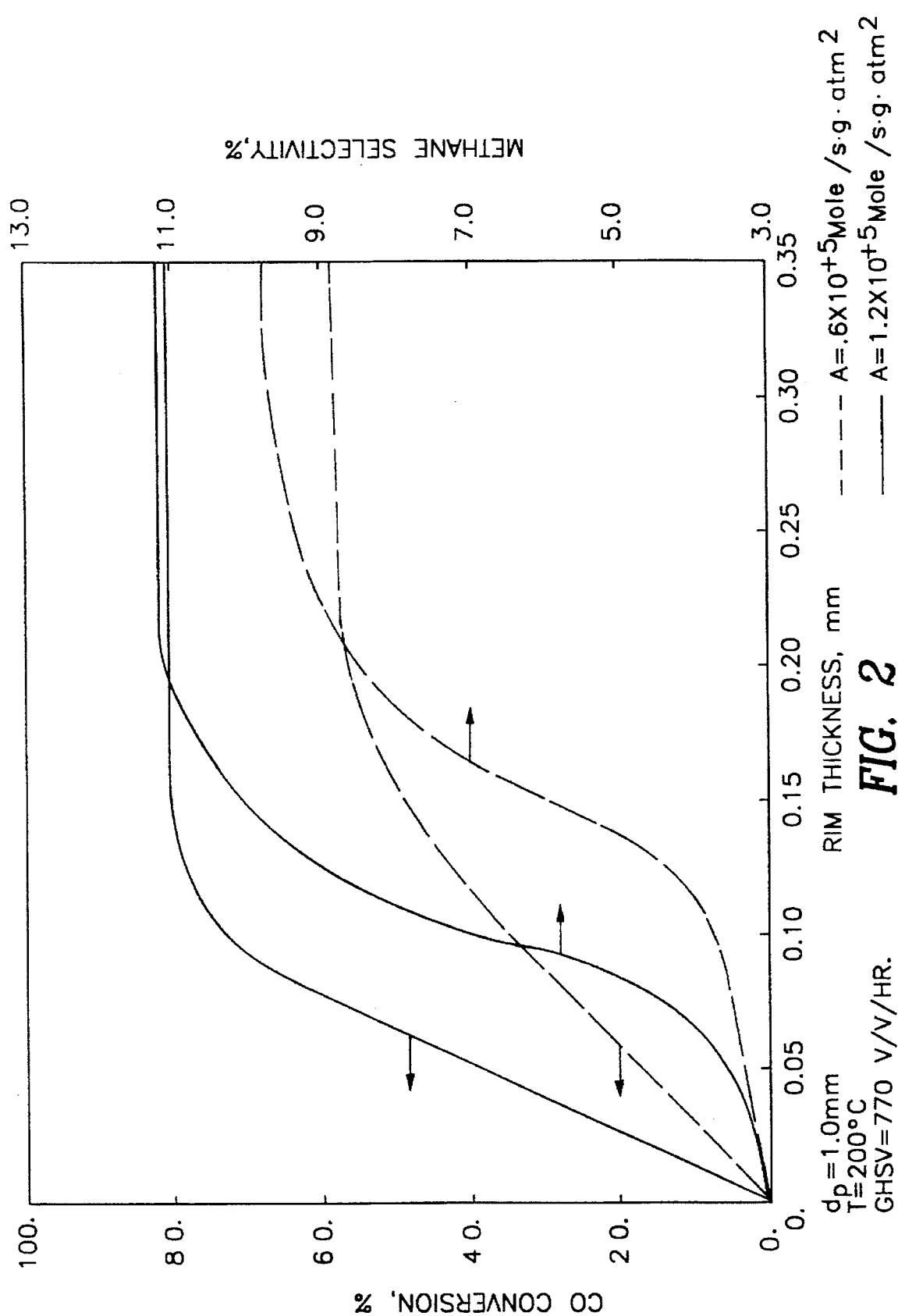
FIG. 2 Shows carbon monoxide conversion and methane selectivity as a function of rim thickness for spherical pellets.
Figure 3:
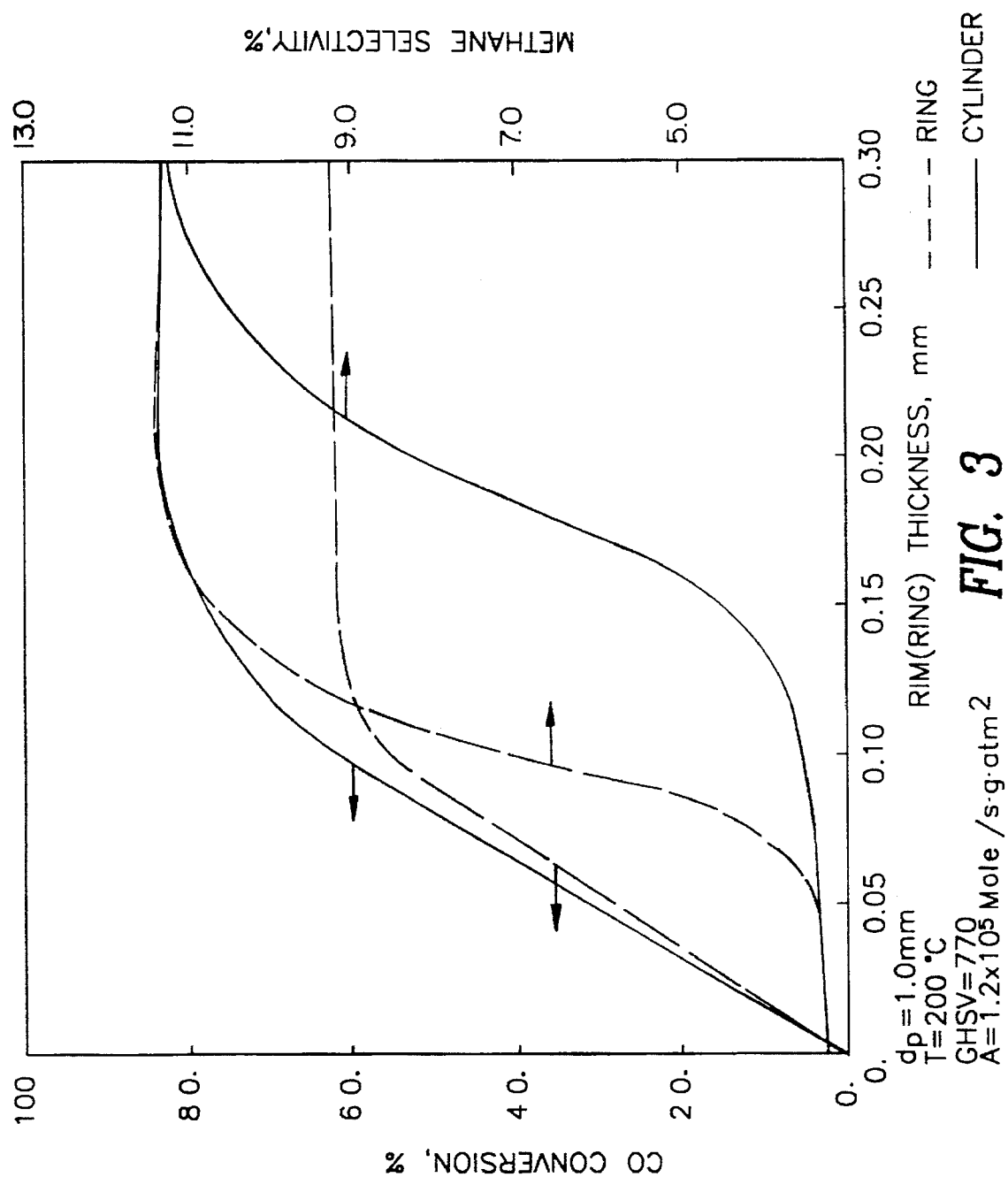
FIG. 3 shows carbon monoxide conversion and methane selectivity as a function of rim thickness for a ring, and cylindrical pellets.

Simulations of the carbon monoxide conversion and methane selectivity as a function of the rim thickness are depicted in FIG. 2 for a spherical pellet loaded with catalysts having two different acivities A hydrogen to Co ratio of 2.0 in the feed was assumed. The carbon monoxide conversion increases with the rim thickness up to is maximum value. The methane selectivity remains almost constant up to certain rim thickness where it increases steeply. Over a range of rim thicknesses the carbon monoxide conversion reaches almost its maximum value while the methane selectivity is still low. Specifically, in FIG. 2 for a spherical pellet with an activity of $6 \times 10^4$ mol/s/g/atm$^2$ the range is 0.13 to 0.15 mm while for an activity of $1.2 \times 10^5$ mol/s/g/atm$^2$ the range is, 0.08 to 0.10 mm. This is the essence of the invention. Based on design, specification, a rim thickness can be determined to give both a high carbon monoxide conversion and a low methane selectivity. The exact value of the rim thickness depends on the catalyst activity, the partial pressures, the temperature and the pellet shape and configuration. An example of a ring and a cylinder is given in FIG. 3. The behavior of those pellet is similar in terms of the effect of rim thickness on CO conversion and methane selectivity. The detailed calculations are carried out for each pellet shape using the general reaction and diffusion model.

EXAMPLE 2

Experiments were performed in a reactor 3 ft. long and 0.5 in. in diameter. The reactor was packed with 1 mm dia. spherical catalyst pellets loaded uniformly with 6% Co–0.5% Re. Isothermal conditions were maintained in the reactor.

Data obtained at various temperatures and hydrogen to CO ratios in the feed were compared with the predictions of the model. As explained previously, the carbon monoxide conversion and methane selectivity were obtained by integrating equations (16) and (17) and calculating the effectiveness factors from equations (13) and (14).

In the experiments with a hydrogen to CO ratio in the feed of less than the stoichiometric ratio (2.07), the ratio decreased along the bed. Since the methane selectivity depends on this ratio, it decreased as the hydrogen to CO ratio decreased. Furthermore, since the diffusion in the catalyst pores was one of the limiting steps in this system, a lower hydrogen to CO ratio increases the parameter γ which means a lower methane selectivity. A comparison of experiments 4, 5 and 6 illustrates the improvements in methane selectivity. In experiment 3, the methane selectivity increased as compared with experiment, 6 because the temperature was higher. The agreement for both the methane selectivity and the carbon monoxide conversion were good, as shown in Table 2.

EXAMPLE 3

Experiments were performed in a reactor 3 feet long and 0.5 inches in diameter. In this case the reactor was operated under nonisothermal conditions, namely the temperature changed along the reactor. The reactor was packed with a spherical rim pellet with 6% Co–0.5% Re catalysts (based on the rim mass). The pellet size, rim thickness and catalyst activity are given in Table 3. The pressure was 20 atm.

The prediction of the carbon monoxide conversion and methane selectivity requires the solution of a heat balance for the reactor along with the mass balances in equations (16) and (17). A comparison of the temperature profiles, CO conversion and methane selectivity are given in Table 3.

The data indicate that the CO conversion is close to the maximum conversion attainable for those pellets under the given conditions (73% and 78% for Experiments, A and B, respectively). However, the methane selectivity was lower than the 11% expected for those pellets as reported in FIG. 1.

The rim tested in this Example was not of optimal size. A 0.1 mm rim would have lowered the methane selectivity to about 5% while keeping the conversion at about 70%.

EXAMPLE 4

Simulations were performed for a pellet of ring shape. The operating conditions assumed in the simulations are:

reactor diameter-1.5"

pellet outer diameter-1.5 mm pellet inner diameter-1.0 mm gas mass velocity-800 lb/ft$^2$/h coolant temperature-347° F.

catalyst activity-1.4×10$^5$ gmol/s/g/atm$^2$ feed composition-64% $H_2$, 32% CO, and 4% $N_2$ The heat balance and the mass balance in equations (16) and (17) were solved to yield the following results:

maximum temperature rise-300° F.

CO conversion-70% methane selectivity-5.6%

TABLE 1

MODEL PREDICTIONS COMPARED WITH DATA

| Pellet Radius | Bulk Density | CO Conversion | |
|---|---|---|---|
| mm | GHSV* | g/cm$^3$ | exp. | pred. |
| 0.088 | 1500 | 1.47 | 76 | 74 |
| 0.166 | 1320 | 1.47 | 76 | 77 |
| 0.252 | 1000 | 1.53 | 78 | 83 |
| 0.356 | 1140 | 1.59 | 73 | 69 |
| 0.500 | 840 | 1.73 | 75 | 76 |
| 0.705 | 510 | 1.64 | 79 | 81 |

*Gas hourly space velocity.

TABLE 2

PREDICTED AND EXPERIMENTAL SELECTIVITIES AND CONVERSIONS

| Exp. No. | Temp., °C. | Feed $H_2$/CO | Selectivity, % exp. | Selectivity, % pred. | CO Conversion, % exp. | CO Conversion, % pred. |
|---|---|---|---|---|---|---|
| 1 | 185 | 1.70 | 6.6 | 4.2 | 48 | 52 |
| 4 | 192 | 2.00 | 9.6 | 8.1 | 76 | 76 |
| 2 | 199 | 1.55 | 6.6 | 5.0 | 56 | 57 |
| 3 | 204 | 1.69 | 8.1 | 7.7 | 63 | 65 |
| 4 | 193 | 2.19 | 10.2 | 10.0 | 74 | 74 |
| 5 | 193 | 1.90 | 7.6 | 7.3 | 74 | 76 |
| 6* | 193 | 1.70 | 5.3 | 4.7 | 74 | 76 |

*The activity decreased by about 10%.

TABLE 3

MODEL PREDICTIONS AGREE WITH NON-ISOTHERMAL PELLET DATA $D_p$ = 1.10 mm
Rim Thick. = 0.15 mm
$H_2$/CO in the feed = 2.0
$k_1$ = 12.0 × 10$^4$ gmol/g/s/atm$^2$

| | EXPERIMENT A | | EXPERIMENT B | |
|---|---|---|---|---|
| | Exp. | Pred. | Exp. | Pred. |
| Co Conv., mol% | 70.6 | 71.6 | 75.3 | 76.6 |
| CH$_4$ Sel., mol% | 8.5 | 8.4 | 8.5 | 8.9 |

| AXIAL POSITION | TEMPERATURE, °F. | | | |
|---|---|---|---|---|
| | TH | TH | TH | TH |
| 0.0 | 377 | | 389 | |
| 0.09 | 383 | 385 | 398 | 401 |
| 0.19 | 385 | 387 | 401 | 403 |
| 0.29 | 388 | 388 | 405 | 405 |
| 0.39 | 390 | 390 | 406 | 406 |
| 0.49 | 390 | 390 | 405 | 405 |
| 0.59 | 390 | 390 | 405 | 404 |
| 0.69 | 388 | 389 | 402 | 402 |
| 0.79 | 387 | 388 | 400 | 399 |
| 0.89 | 385 | 387 | 397 | 397 |
| 0.99 | 381 | 385 | 393 | 395 |

What is claimed is:

1. A method for making a CO hydrogenation catalyst wherein said catalyst includes a metal selected from the group consisting of cobalt and ruthenium deposited in a porous, inorganic, refractory oxide support, said catalyst having said metal located in a rim on the outer surface of said support, said method comprising:

(a) determining the rim thickness by
      (i) determining intrinsic kinetic rate data including the intrinsic rate of reaction of carbon monoxide hydrogenation and the rate of CO conversion to methane for said catalyst;
      (ii) determining the thickness of said rim by relating the rates of diffusion of said carbon monoxide and said hydrogen to the intrinsic rate of reaction in said rim for a support geometry selected from the group consisting of a sphere, a ring, a cylinder, and a semi-circle and combinations thereof, such that said rim thickness optimizes both the rate of carbon monoxide hydrogenation and the reduction in methane selectivity; and
   (b) making a catalyst having a rim thickness determined in step (a).

2. The process of claim 1 wherein said rim thickness is less than 0.20 mm.

3. The process of claim 1 wherein said catalyst pellet has a shape selected from the group consisting of a sphere, a ring, a cylinder, and a semi-circle.

4. The process of claim 1 including applying a promoter material selected from the group consisting of rhenium and hafnium to said rim.

5. The process of claim 1 wherein said porous, inorganic refractory oxide is selected from the group consisting of titania, silica, and alumina.

* * * * *